(12) United States Patent
Cahill et al.

(10) Patent No.: US 7,759,068 B2
(45) Date of Patent: Jul. 20, 2010

(54) USE OF SUBSTANCES FOR TREATING TUMORS

(75) Inventors: Michael Cahill, Loerzweiler (DE); Wojciech Wozny, Nieder-Olm (DE); André Schrattenholz, Mainz (DE); Helmut Klocker, Inzing (AT); Hermann Rogatsch, Klagenfurt (AT)

(73) Assignee: Proteosys AG, Mainz (DE)

( * ) Notice: Subject to any disclaimer, the term of this patent is extended or adjusted under 35 U.S.C. 154(b) by 45 days.

(21) Appl. No.: 10/511,205

(22) PCT Filed: Apr. 15, 2003

(86) PCT No.: PCT/EP03/03892

§ 371 (c)(1),
(2), (4) Date: Feb. 15, 2005

(87) PCT Pub. No.: WO03/086461

PCT Pub. Date: Oct. 23, 2003

(65) Prior Publication Data

US 2005/0130876 A1      Jun. 16, 2005

(30) Foreign Application Priority Data

Apr. 15, 2002 (DE) ............................ 102 17 254

(51) Int. Cl.
*G01N 33/53* (2006.01)
(52) U.S. Cl. ...................................................... 435/7.1
(58) Field of Classification Search .................. 435/4, 435/7.1
See application file for complete search history.

(56) References Cited

U.S. PATENT DOCUMENTS

| 5,236,844 | A | 8/1993 | Basset et al. |
| 5,856,330 | A | 1/1999 | Mullner et al. |
| 6,030,824 | A | 2/2000 | Hillman et al. |
| 6,034,218 | A | 3/2000 | Reed et al. |
| 2003/0152565 | A1 | 8/2003 | Bartorelli |

FOREIGN PATENT DOCUMENTS

| CN | 1315580 | | 10/2001 |
| EP | 0 821 960 | A | 7/1997 |
| WO | WO 99/22729 | | 5/1999 |
| WO | WO 01/46250 | A | 6/2001 |
| WO | WO 01/72791 | A | 10/2001 |
| WO | 01/90376 | | 11/2001 |
| WO | WO 01/88158 | A | 11/2001 |
| WO | WO 01/94376 | A | 12/2001 |
| WO | WO 02/009748 | A | 2/2002 |
| WO | 02/20731 | A2 | 3/2002 |

OTHER PUBLICATIONS

Blankenberg et al, PNAS, May 1998, 95: 6349-6354.*
Tockman et al (Cancer Res., 1992, 52:2711s-2718s).*
Cher and Carroll (1995, West J Med, 162:235-242).*
Bukkapatnam, R. et al. "Radical Prostatectomy in the Management of Clinically Localized Prostate Cancer", *Cancer Control*, vol. 8 (6) pp. 496-502, 2001.
Waghray, A. et al. "Identification of Differentially Expressed Genes by Serial Analysis of Gene Expression in Human Prostate Cancer", Cancer Research, vol. 61 pp. 4283-4286, 2001.
Magee, J.A. et al. "Expression Profiling Reveals Hepsin Overexpression in Prostate Cancer", *Cancer Research*, vol. 61 pp. 5692-5696, 2001.
Welsh, J.B. et al. "Analysis of Gene Expression Identifies Candidate Markers and Pharmacological Targets in Prostate Cancer", *Cancer Research*, vol. 61 pp. 5974-5978, 2001.
Rini, B.I. et al. "Immunotherapy for Prostate Cancer", *Current Oncology Reports*, vol. 3 pp. 418-423, 2001.
Heidenreich, A. et al. "Current Status of Cytotoxic Chemotherapy in Hormone Refractory Prostate Cancer", *Eur Urol*, vol. 39 pp. 121-130, 2001.
Eder, I.E. et al. "Molecular Biology of the Androgen Receptor: From Molecular Understanding to the Clinic", *Eur Urol*, vol. 40 pp. 241-251, 2001.
Miyake, H. et al. "Novel therapeutic strategy for advanced prostate cancer using antisense oligodeoxynucleotides targeting anti-apoptotic genes unregulated after androgen withdrawl to delay androgen-independent progression and enhance chemosensitivity", International Journal of Urology, vol. 8 pp. 337-349, 2001.
Afrin, L.B. et al. "Medical Therapy of Prostate Cancer: 1999", *The Journal of the South Carolina Medical Association*, vol. 96 pp. 77-84, 2000.
Stamey, T.A. et al. "Molecular Genetic Profiling of Gleason Grade 4/5 Prostate Cancers Compared to Benign Prostatic Hyperplasia", The Journal of Urology, vol. 166 pp. 2171-2177, 2001.
Pentyala, S.N. et al. "Prostate Cancer: a comprehensive review", Medical Oncology, vol. 17 pp. 85-105, 2000.
Dhanasekaran, S.M. et al. "Delineation of prognostic biomarkers in prostate cancer", NATURE, vol. 412 pp. 822-826, 2001.
Chaib, H. et al. "Profiling and Verification of Gene Expression Patterns in Normal and Malignant Human Prostate Tissues by cDNA Microarray Analysis", Neoplasia, vol. 3 (1) pp. 43-52, 2001.
DiPaola, R.S. et al. "State-of-the-Art Prostate Cancer Treatment and Research- A Report from The Cancer Institute of New Jersey", New Jersey Medicine, vol. 98 pp. 23-33, 2001.
Auclerc, G. et al. "Management of Advanced Prostate Cancer", *The Oncologist*, vol. 5 pp. 36-44, 2000.
Hussain, A. et al. "Management of Advanced/Metastatic Prostate Cancer: 2000 Update", Oncology, vol. 14 (12), 2000.
Chetcuti, A. et al. "Identification of Differentially Expressed Genes in Organ-Confined Prostate Cancer by Gene Expression Array", The Prostate, vol. 47 pp. 132-140, 2001.
Crawford, E.D. et al. "Overview: Hormone Refractory Prostate Cancer", *Urology*, vol. 54 pp. 1-7, 1999.

(Continued)

*Primary Examiner*—Sean E Aeder
(74) *Attorney, Agent, or Firm*—The Nath Law Group; Joshua B. Goldberg; Tanya E. Harkins

(57) ABSTRACT

The present invention relates to the use of an active ingredient and to a method for the prevention or treatment of tumors, the diagnostic detection of disorders associated with these tumors, and pharmaceutical compositions and kits related thereto.

Figure 1:
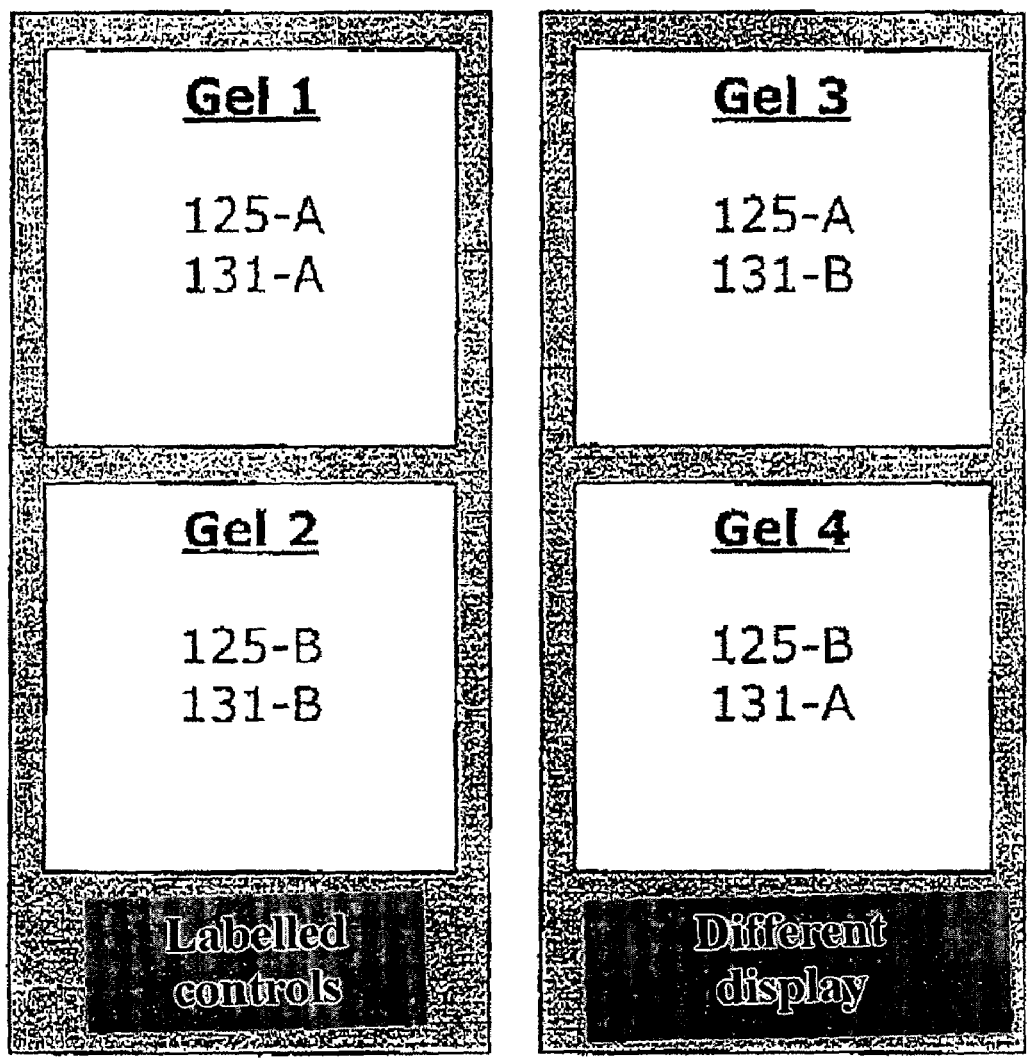

1 Claim, 5 Drawing Sheets
(3 of 5 Drawing Sheet(s) Filed in Color)

OTHER PUBLICATIONS

Bartsch, G. et al. "Prostate Cancer Mortality After Introduction of Prostate-Specific Antigen Mass Screening in the Federal State of Tyrol, Austria", Urology, vol. 58 (3) pp. 417-424, 2001.

Jianlin et al., "Construction, Expression and Space Conformation Analysis of Anti-Human γ-Seminoprotein $V_H$ Single Domain Antibody Gene", *J. of Xi' An Med. Univ.*, vol. 22, pp. 197-200, 2001.

(XP-002246985) Lindquist, J.A., et al., "ER-60, a chaperone with thiol-dependent reductase activity involved in MHC assembly", *The EMBO Journal*, vol. 17, No. 8, pp. 2186-2195, (1998).

(XP-001122363) Petrie III et al., "Synthesis of analogs of N-acetylneuraminic acid and their effect on CMP-sialate synthase," Carbohydrate Research, 186: 326-334 (1989).

(XP-002104552) Alaiya et al., "Phenotypic Analysis of Ovarian Carcinoma: Polypeptide Expression in Benign, Borderline and Malignant Tumors," International Journal of Cancer, 73:678-683 (1997).

(XP-002298703) Almond et al., "The Proteasome: a novel target for cancer chemotherapy," Leukemia, 16:433-443 (2002).

(XP-002389495) Lawrence et al., "Cloning and Expression of the Human N-Acetylneuraminic Acid Phosphate Synthase Gene with 2-Keto-deoxy-D-*glycero*-D-*galacto*-nononic Acid Biosynthetic Ability," The Journal of Biological Chemistry, vol. 275, pp. 17869-17877 (Jun. 9, 2000).

(XP-002389496) Ou et al., "Proteome analysis of a human heptocellular carcinoma cell line, HCC-M: An Update," Electrophoresis, 22:2804-2811 (2001).

(XP-002389497) Kim et al., "Expression of a functional *Drosophila melanogaster N-acetylneuraminic acid* (Neu5Ac) phosphate synthase gene: evidence for endogenous sialic acid biosynthetic ability in insects," Glycobiology, vol. 12, No. 2, pp. 73-83 (2002).

(XP-002389498) Zeng et al., "Suppression of Ganglioside GD3 Expression in a Rat F-11 Tumor Cell Line Reduces Tumor Growth, Angiogenesis, and Vascular Endothelial Growth Factor Production," Cancer Research, 60:6670-6676 (Dec. 1, 2000).

(XP-002389499) Miura et al., "Application of L-Threonine Aldolase-Catalyzed Reaction to the Preparation of Protected 3R, 5R, Dihydroxy-L-homoproline as a Mimetic of Idulonic Acid," Chirality 13:577-580, (2001).

(XP-002389500) Wilk et al., "Properties of the Beta Subunit of the Proteasome Activator PA28 (11S REG)," Archives of Biochemistyr and Biophysics, vol. 384, No. 1, pp. 174-180 (2000).

(XP-002389501) Stohwasser et al., "PA28αβ double and PA28β single transfectant mouse B8 cell lines reveal enhanced presentation of a mouse cytomegalovirus (MCMV) pp89 epitope," Molecular Immunlogy, 37:13-19 (2000).

(XP-002389502) Pieper et al., "Biochemical Identification of a Mutated Human Melanoma Antigen Recognized by CD4+ T Cells," The Journal of Experimental Medicine, vol. 189, No. 5, pp. 757-765 (1999).

(XP-002389518) Norman et al., "Purification and Characterization of Phosphoglycolate Phosphatase from the Cyanobacterium Coccochloris peniocystis," Plant Physiology, 95:693-698 (1991).

(XP-002389519) Nagamine, et al., "Isolation of cDNA for a Novel Human Protein KNP-1 That is Homologous to the *E. coli* SCRP-27A Protein from the Autoimmune Polyglandular Disease Type 1 (APECED) Region of Chromosome 21q22.3," Biochemical and Biophysical Research Communications, 225:608-616 (1996).

(XP-002389520) Park et al., "Mapping of a new target region of allelic loss at 21q22 in primary gastric cancers," Cancer Letters, 159:15-21 (2000).

(XP-002389521) Kanai et al., "mRNA expression of genes altered by 5-azacytidine treatment in cancer cell lines is associated with clinicopathological parameters of human cancers," Journal of Cancer Research and Clinical Oncology, 127:697-706 (2001).

(XP-002389522) Zebda et al., "Phosphorylation of ADF/Cofilin Abolishes EGF-induced Actin Nucleation at the Leading Edge and Subsequent Lamellipod Extension," The Journal of Cell Biology, vol. 151, No. 5, pp. 1119-1127 (2000).

(XP-00238928—Attaching WO 01/88158 A) Database WPI; Derwent Publications Ltd.; Nov. 22, 2001.

(XP-002389529) Database WPI; Derwent Publications Ltd.; Oct. 3, 2001.

(XP-002389530—Attaching WO 01/94376 A) Database WPI; Derwent Publications Ltd.; Nov. 29, 2001.

(XP-002389531—Attaching WO 01/46250 A) Database WPI; Derwent Publications Ltd.; Jul. 3, 2001.

(XP-002389532—Attaching WO 01/72791 A) Database WPI; Derwent Publications Ltd.; Oct. 4, 2001.

(XP-002967640) Gillet et al., "Mapping of human non-muscle type cofilin (CFL1) to chromosome 11q13 and muscle-type cofilin (CFL2) to chromosome 14," Annotated Human Genetics, 60:201-211 (1996).

(XP-009068792) Hadfield et al., "N-Acetyl-D-Mannosamine Analogues as Potential Inhibitors of Sialic Acid Biosynthesis," Journal of Pharmaceutical Scuences, vol. 72, No. 7 (Jul. 1983).

(XP-009068954) Nobuo Matsuzuka, "Experimental and Clinical Studies on Triosephosphate Isomerase and its Isoenzymes," Hokkaido Journal of Medical Science, vol. 52, No. 5, pp. 439-455 (1977).

(XP-009069171) Beck et al., "Cloning of contiguous genomic fragments from human chromosome 21 harbouring three trefoil peptide genes," Human Genetics, 98:233-235 (1996).

Angelino et al., "Versatile intermediates in the selective modification of the amino function of 2-amino-2-deoxy-D-mannopyranose and the potential membrane modifiers in neoplastic control," Carbohydrate Research, 276:99-115 (1995).

Liu et al., "Comparison of chemical and enzymatic synthesis of 2-acetamido-2-deoxy-D-mannose 6-phosphate: a new approach," Carbohydrate Research, 330:413-419 (2001).

Schuuring, Ed, "The involvement of the chromosome 11q13 region in human malignancies: *cyclin D1* and *EMS1* are two new candidate oncogenes—a review," Genetics, 159:83-96 (1995).

* cited by examiner

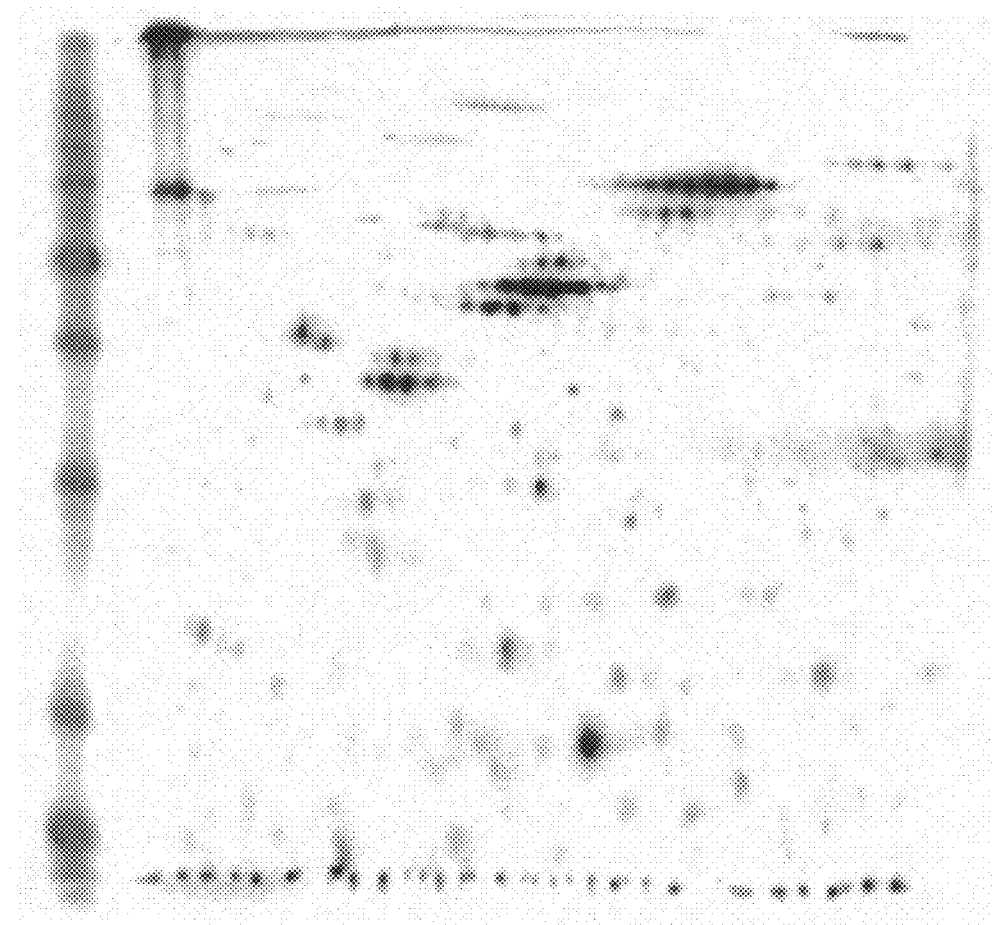

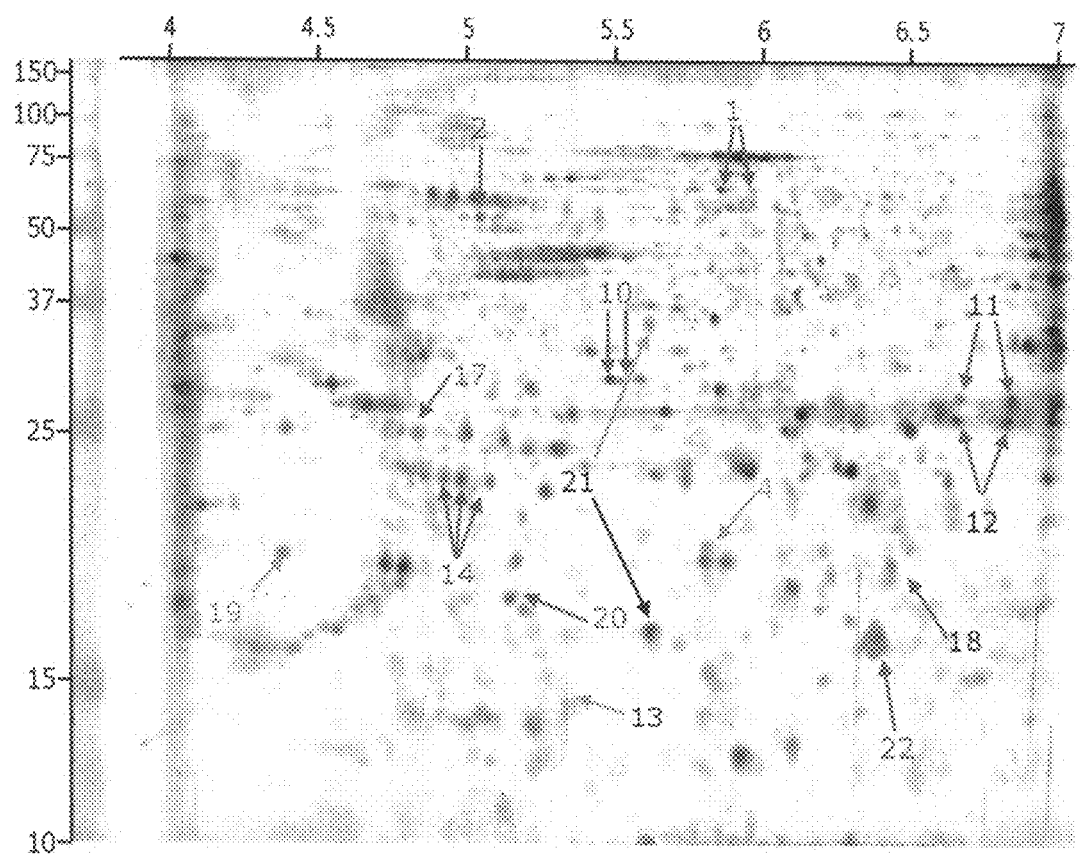

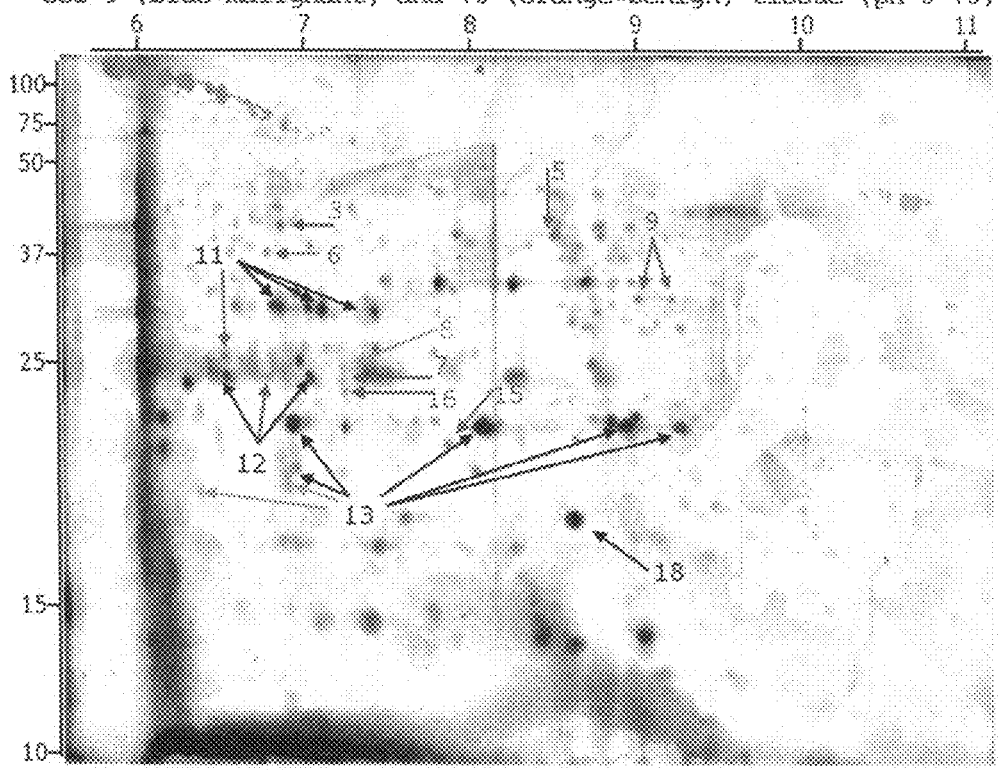

SEQUENCE LISTING

```
<160> NUMBER OF SEQ ID NOS: 2

<210> SEQ ID NO 1
<211> LENGTH: 359
<212> TYPE: PRT
<213> ORGANISM: Homo sapiens

<400> SEQUENCE: 1

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
        35                  40                  45

Asp Cys Ala Lys Phe Gln Lys Ser Glu Leu Glu Phe Lys Phe Asn Arg
    50                  55                  60

Lys Ala Leu Glu Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
            100                 105                 110

Gly Met Asp Glu Met Ala Val Glu Phe Leu His Glu Leu Asn Val Pro
        115                 120                 125

Phe Phe Lys Val Gly Ser Gly Asp Thr Asn Asn Phe Pro Tyr Leu Glu
    130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Phe Leu Gln Cys Thr Ser Ala Tyr Pro Leu Gln Pro
            180                 185                 190
```

```
Glu Asp Val Asn Leu Arg Val Ile Ser Glu Tyr Gln Lys Leu Phe Pro
        195                 200                 205

Asp Ile Pro Ile Gly Tyr Ser Gly His Glu Thr Gly Ile Ala Ile Ser
        210                 215                 220

Val Ala Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
                245                 250                 255

Gly Glu Leu Ala Glu Leu Val Arg Ser Val Arg Leu Val Glu Arg Ala
            260                 265                 270

Leu Gly Ser Pro Thr Lys Gln Leu Pro Cys Glu Met Ala Cys Asn
        275                 280                 285

Glu Lys Leu Gly Lys Ser Val Ala Lys Val Lys Ile Pro Glu Gly
        290                 295                 300

Thr Ile Leu Thr Met Asp Met Leu Thr Val Lys Val Gly Glu Pro Lys
305                 310                 315                 320

Gly Tyr Pro Pro Glu Asp Ile Phe Asn Leu Val Gly Lys Lys Val Leu
                325                 330                 335

Val Thr Val Glu Glu Asp Asp Thr Ile Met Glu Glu Leu Val Asp Asn
                340                 345                 350

His Gly Lys Lys Ile Lys Ser
        355

<210> SEQ ID NO 2
<211> LENGTH: 195
<212> TYPE: PRT
<213> ORGANISM: Homo sapiens

<400> SEQUENCE: 2

Met Ala Ala Val Arg Val Leu Val Ala Ser Arg Leu Ala Ala Ala Ser
1               5                   10                  15

Ala Phe Thr Ser Leu Ser Pro Gly Gly Arg Thr Pro Ser Gln Arg Ala
                20                  25                  30

Ala Leu His Leu Ser Val Pro Arg Pro Ala Ala Arg Val Ala Leu Val
            35                  40                  45

Leu Ser Gly Cys Gly Val Tyr Asp Gly Thr Glu Ile His Glu Ala Ser
        50                  55                  60

Ala Ile Leu Val His Leu Ser Arg Gly Ala Glu Val Gln Ile Phe
65                  70                  75                  80

Ala Pro Asp Val Pro Gln Met His Val Ile Asp His Thr Lys Gly Gln
                85                  90                  95

Pro Ser Glu Gly Glu Ser Arg Asn Val Leu Thr Glu Ser Ala Arg Ile
            100                 105                 110

Ala Arg Gly Lys Ile Thr Asp Leu Ala Asn Leu Ser Ala Ala Asn His
        115                 120                 125

Asp Ala Ala Ile Phe Pro Gly Gly Phe Gly Ala Ala Lys Asn Leu Leu
    130                 135                 140

Cys Cys Ile Ala Pro Val Leu Ala Ala Lys Val Leu Arg Gly Val Glu
145                 150                 155                 160

Val Thr Val Gly His Glu Gln Glu Gly Gly Lys Trp Pro Tyr Ala
                165                 170                 175

Gly Thr Ala Glu Ala Ile Lys Ala Leu Gly Ala Lys His Cys Val Lys
            180                 185                 190

Glu Val Val
        195
```

USE OF SUBSTANCES FOR TREATING TUMORS

The present invention relates to the use of an active ingredient and to a method for the prevention or treatment of tumors, the diagnostic detection of disorders associated with these tumors, and pharmaceutical compositions and kits related thereto.

By tumor is meant a swelling or the localized increase in tissue volume. In the wider sense it may mean any localized swelling, e.g. through an edema, an acute or chronic inflammation, aneurysmal dilatation, an inflammation-related organ swelling (e.g. a so-called splenic enlargement). In the narrower sense, tumor means tissue neoplasms (growth, blastoma, neoplasia) in the form of a spontaneous, autonomous and irreversible excessive growth, with various degrees of disinhibition, of endogenous tissue, which is usually associated with various degrees of loss of specific cellular and tissue function.

Tumors are divided for better classification into:
I. According to their Biological Behavior:
  1. Benign tumors with differentiated cells and slow, locally displacing growth.
  2. Malignant tumors with cell nuclear polymorphism, cell atypia, anaplasia and infiltrating, usually rapid, destructive growth and metastasis.
  3. Semimalignant tumors with the histological characteristics of malignant tumors and locally infiltrating growth, but usually without metastasis.
II. Histogenic Classification:
This entails the tumors being classified on the basis of the tissue from which they have originated in the developmental history. There are:
  1. Epithelial tumors originating from ectoderm and entoderm:
    a) benign tumors such as, for example, adenoma, papilloma and polyps
    b) malignant tumors such as, for example, carcinoma.
  2. Mesenchymal tumors originating from the mesoderm:
    a) benign tumors, such as, for example, lipoma, fibroma, osteoma, myoma, leiomyoma, rhabdomyoma, chondroma,
    b) malignant tumors such as, for example, the sarcomas.
  3. Embryonic tumors have originated from undifferentiated tissue. These include for example nephroblastomas, neuroblastomas, medulloblastomas, retinoblastomas and embryonic rhabdomyosarcomas and teratomas.
III. Classification According to Clinical and Pathological Findings:
  Inter alia the TNM classification, grading, Laurén classification, Dukes classification, Kieler classification, Rappaport classification etc apply here.

Even this brief review of tumor classification shows the diversity (and in some cases antagonism) existing within the various types of tumors. Thus, for example, a distinction is to be made not only between benign and malignant tumors but also between mortality or lethality of the individual tumors and the probability that a benign tumor develops further to a malignant tumor.

Some tumors such as, for example, breast carcinomas (breast cancer), the commonest malignant tumor of women, occur with increased frequency in particular between the ages of 45 and 70. Early symptoms are suspicious findings of palpation, which are usually discovered following the examinations for early cancer diagnosis and on regular self-examination of the breast. Depending on the tumor stage and degree of differentiation of the tumor, the prognosis in these cases may range from definitely positive to very poor. As a consequence of the early lymphogenous and hematogenous metastasis of breast carcinomas it is important for the tumor to be diagnosed rapidly in order to be able to institute therapy as early as possible.

Prostatic carcinomas (carcinoma of the prostate) is on the other hand the commonest malignant tumor in men, which occurs in particular between the ages of 50 and 70. They are in most cases adenocarcinomas. This malignant tumor initially spreads through infiltrating growth within the prostate, and later there is infiltration of vesicular glands and pelvic connective tissue, and relatively rarely of the rectum, bladder or urethra. Lymphogenous and/or hematogenous metastasis takes place. The therapy depends on the histological degree of differentiation and clinical stage and usually involves radical prostatectomy with regional lymph node extirpation, and in the advanced stage withdrawal of male sex hormones. In these cases, too, the prognosis depends on the stage of the carcinoma. Whereas in a very early stage a radical prostatectomy is followed by cure in about 90% of cases, in an advanced stage the prognosis tends to be pessimistic.

Prostatic carcinomas need to be diagnostically differentiated from hyperplasia of the prostate. Hyperplasia of the prostate is a benign tumor. In these cases there is enlargement of the prostate through a numerical increase in cells and glands of the stroma. Hyperplasia of the prostate is the commonest cause of impairments of bladder emptying in men. Its clinical onset is in particular between the ages of 40 and 50. Progression is slow and episodic. Moreover, symptoms in most cases appear only after some years with a gradual weakening of the urinary stream and delayed start of urination. In these cases, the administration of phytotherapeutic agents may be considered as therapy or alleviation of the symptoms.

Since early recognition, i.e. diagnosis, of tumors is generally important for starting therapy quickly, and the prognosis is also better when the tumor is diagnosed earlier, a number of so-called tumor markers are in clinical use. Substances and cellular changes whose qualitative or quantitative analysis may enable statements to be made about the presence, progression or prognosis of (malignant) disorders are generally referred to as tumor markers. Tumor markers are classified as:

1. Cellular Tumor Markers:
  These include inter alia cell membrane-associated tumor antigens, receptors (e.g. hormone receptors, receptors for growth-promoting substances in leukemia) and cell markers which indicate an increased expression of oncogenes and a monoclonal cell growth, and molecular genetic cellular changes, especially chromosome aberrations.

2. Humoral Tumor Markers:
  These are (usually physiologically occurring) substances which are detectable in increased concentrations, compared with physiological conditions, in serum, urine and other body fluids and which are synthesized and/or secreted by the tumor tissue, released by oncolysis or formed as a response of the organism to a tumor. The physiological significance of tumor markers is only inadequately known. They usually have no immunogenic effect in the human body. The clinical (diagnostic) significance depends on their specificity and sensitivity. The humoral tumor markers are divided into two groups. The first group comprises the humoral tumor markers which are produced by the tumor itself. These include, for example, tumor-associated antigens, certain hormones (e.g. gastrin, cortisol etc), enzymes (e.g. neuron-specific enolase (NSE)), and proteins (e.g. Bence-Jones protein). The second group comprises the tumor markers which, although induced by the tumor, are not produced by it. Important humoral tumor markers of this group are, for example, alkaline phosphatase (AP), LDH, neopterin etc.

The statements made above show how important selective and sensitive tumor detection methods are. There is in addition a great need for novel targets for tumor therapy.

Accordingly, the object of the invention is to provide novel active ingredients and targets for diagnostic and therapeutic applications in tumor therapy.

It has surprisingly been possible to show in experiments with various tumors that certain proteins were synthesized and/or secreted only in the tissue affected by tumors. These proteins thus play an important role in the development of tumors and the progression of a neoplastic disease.

Accordingly, the object of the invention is achieved by the subject matter of independent claims 1 to 5, 14, 18 and 22. Preferred embodiments are specified in the dependent claims 6 to 13, 15 to 17, 19 to 21 and 23. The content of all these claims is hereby included in the description by reference.

It is possible according to the invention to use at least one active ingredient for the prevention or treatment of tumors, in particular malignant tumors. In this connection, this active ingredient influences the expression and/or the function of proteins synthesized and/or secreted by the tumor in eukaryotic cells, whereby the increase in tissue volume and/or metastasis of the tumor is at least partially inhibited. By influencing the expression and/or function of the proteins synthesized and/or secreted by the tumor is meant in particular inhibition of these proteins. This active ingredient can further be used to produce a medicament or a pharmaceutical composition for the prevention or treatment of tumors.

Also claimed is the use of a substance for detecting the expression and/or the function of proteins synthesized and/or secreted by tumors, in particular malignant tumors, in eukaryotic cells, for diagnosing disorders associated with these tumors. Disorders associated with these tumors include, for example, the abovementioned prostatic carcinomas, hyperplasia of the prostate (hypertrophy of the prostate) etc. However, all other tumor-associated disorders in which the proteins of the invention are synthesized and/or secreted are also encompassed by the invention.

In a further preferred embodiment, a method for the prevention or treatment of tumors, in particular malignant tumors, is claimed, where eukaryotic cells are treated with an active ingredient which influences, in particular inhibits, the expression and/or the function of proteins synthesized and/or secreted by tumors, and thus at least partially inhibits the increase in tissue volume and/or the metastasis of the tumors.

In addition, in a further preferred embodiment, a method for diagnosing disorders associated with tumors, in particular malignant tumors, is claimed, where eukaryotic cells are brought into contact with a substance which detects the expression and/or the function of proteins synthesized and/or secreted by these tumors.

The proteins synthesized and/or secreted by the tumors may be, in a particularly preferred embodiment, the proteins listed in table I shown below. Thus, the substance employed for detecting and/or for diagnosing tumor-associated disorders may be for example an antibody which is directed against these proteins and is employed in a detection method known to the skilled worker, such as, for example, ELISA (enzyme-linked immuno sorbent assay). In such so-called immunoassays, the specific antibody directed against the antigen to be determined (or in the case of antibody determinations homologous test antigens) is bound to a support substance (e.g. cellulose, polystyrene) on which immune complexes form after incubation with the sample. In a subsequent step, a labeled antibody is added to these immune complexes. It is possible, by adding a homogeneous substrate to the reaction mixture, to visualize the immune complex-bound enzyme-substrate complexes and estimate the antigen concentration in the sample via a photometric determination of the immune complex-bound marker enzymes by comparison with standards of known enzymic activity. Further substances which can be used for the diagnostic detection are, for example, so-called oligonucleotides which are suitable, with the aid of the so-called polymerase chain reaction (PCR), via a molecular genetic method in which there is selective amplification of particular DNA segments, for achieving quantitative detection of the investigated proteins. Further methods allowing a known target protein to be detected quantitatively or qualitatively are familiar to the skilled worker. Active ingredients which can be used for at least partial inhibition of these proteins are likewise known to the skilled worker. Thus, for example, so-called antisense sequences can be used as active ingredient. It is additionally possible to use genetically modified mutants of these proteins according to the invention as active ingredient, e.g. so-called deficient mutants in which the enzymatic activity has been eliminated. Protein NM_018946, Sialic acid synthase, identified by accession number gi 12056473 and shown in row 6 of Table 1 corresponds to SEQ ID NO: 1. Protein AB_001517, KNP-I beta, identified by accession number gi_2250701 and shown in row 16 of Table 1 corresponds to SEQ ID NO: 2.

TABLE I

Detected tissue-specific proteins

| | Acc no | Protein | Scores | MW Theo. | MW range | pI | Expr. cancer |
|---|---|---|---|---|---|---|---|
| 1 | gi|1085373 | protein disulfide-isomerase EC 5.3.4.1) ER60 precursor - human | 319 | 57883 | 60000 | 5.9 6.1 | ++ ++ |
| 2 | gi|1374715 | ATP synthase beta chain, mitochondrial precursor | 284 | 56525 | 55000 | 5.0 | ++ |
| 3 | gi|14729950 | (XM_028869) isocitrate dehydrogenase 1 (NADP+), soluble [*Homo sapiens*] | 94 | 47515 | 42000 | 6.8 | ++ |
| 4 | gi|184326 | M12387) haptoglobin precursor [*Homo sapiens*] | 100 | 47073 | 22000 | 5.8 | + |
| 5 | gi|4505763 | (NM_000291) phosphoglycerate kinase 1 [*Homo sapiens*] | 136 | 45826 | 40000 | 8.7 | ++ |
| 6 | gi|12056473 | (NM_018946) N-acetylneuraminic acid phosphate | 167 | 41698 | 37000 | 6.5 | ++ |

TABLE I-continued

Detected tissue-specific proteins

| Acc no | Protein | Scores | MW Theo. | MW range | pI | Expr. cancer |
|---|---|---|---|---|---|---|
| 7 gi\|13111901 | synthase, sialic acid synthase, sialic acid phosphate (BC003119) Similar to ATP synthase, H+ transporting, mitochondrial F1 complex, alpha subunit, isofo | 76 | 40614 | 25000 | 7.1 | ++ |
| 8 gi\|4757756 | (NM_004039) annexin A2, annexin II, lipocortin II, Annexin II (lipocortin I), calpactin I, heavy po | 81 | 39288 | 25000 | 7.1 | -- |
| 9 gi\|5174541 | (NM_005918) malate dehydrogenase 2, NAD (mitochondrial), Malate dehydro-genase, mitochondrial | 177 | 36925 | 32000 32000 | 9.2 9.5 | ++ ++ |
| 10 gi\|4506237 | (NM_002818) proteasome (prosome, macropain) activator subunit 2 (PA28 beta), Proteasome activator s | 96 | 27863 | 30000 30000 | 5.5 5.6 | o ++ |
| 11 gi\|225915 | gamma seminoprotein [Homo sapiens] | 120 | 27843 | 25000 25000 32000 32000 32000 | 6.5 6.8 6.8 7.1 7.5 | ++ ++ o o o |
| 12 gi\|999892 | Chain A, Triosephosphate Isomerase (Tim) (E.C.5.3.1.1) Complexed With 2-Phosphoglycolic Acid | 200 | 27407 | 25000 25000 25000 | 6.5 6.8 7.1 | + + o |
| 13 gi\|4507359 | (NM_003186) transgelin; smooth muscle protein 22-alpha; 22 kDa actin-binding protein; SM22-alpha | 100 | 22638 | 15000 20000 20000 21000 23000 23000 23000 23000 | 5.3 6.6 6.1 6.6 6.9 8.2 9.1 9.6 | - - -- -- o o o + |
| 14 gi\|5729842 | (NM_006708) glyoxalase I, lactoyl glutathione lyase, lactoylglutathione lyase [Homo sapiens] | 135 | 21415 | 22000 22000 22000 | 4.8 4.9 5.0 | ++ ++ ++ |
| 15 gi\|4505621 | (NM_002567) prostatic binding protein, phosphatidylethanolamine binding protein [Homo sapiens] | 160 | 21398 | 20000 | 7.9 | + |
| 16 gi\|2250701 | (AB001517) KNP-I beta protein [Homo sapiens] | 68 | 20819 | 25000 | 7.1 | ++ |
| 17 gi\|4827038 | (NM_005079) tumor protein D52 [Homo sapiens] | 131 | 19851 | 25000 | 4.7 | ++ |
| 18 gi\|5031635 | (NM_005507) cofilin 1 (non-muscle) [Homo sapiens] | 125 | 19199 | 17000 18000 | 8.5 6.5 | o ++ |
| 19 gi\|4507387 | (NM_003197) transcription elongation factor B polypeptide 1-like, organ of Corti protein 2 [Homo sapiens] | 74 | 19177 | 18000 | 4.2 | - |
| 20 gi\|4503545 | (NM_001970) eukaryotic translation initiation factor 5A [Homo sapiens] | 102 | 17530 | 17000 | 5.1 | + |
| 21 gi\|10120703 | Chain A, Structure of Human Transthyretin Complexed With Bromophenols: A New Mode Of Binding | 164 | 13930 | 17000 37000 | 5.6 5.6 | ++ o |
| 22 gi\|4557581 | Fatty acid binding protein 5 (psoriasis-associated) | 60* | 15155 | 18000 | 6.5 | ++ |

Scores = hits found with the aid of the MASCOT technique
MW theo. = theoretical (calculated) molecular weight
MW range = found in the molecular weight range of the indicated marker proteins
pI = isoelectric point
Expr. cancer (o = found both in malignant and benign tissue; + upregulated; − downregulated).

In a further preferred embodiment, the active ingredient or the substance is directed against the proteins themselves which are synthesized and/or secreted by the tumors. As already described, the active ingredients may be for example antisense sequences. These are then directed directly against the synthesized and/or secreted proteins. The active ingredient may additionally constitute genetically modified mutants. Thus, it is possible to construct, for example, by genetic engineering methods, mutants in which the catalytic center is eliminated (so-called deficient mutants). In these cases, although the tumor-associated proteins are synthesized, they have no or only a reduced enzymatic activity. These deficient mutants which have previously been inserted into the tumor tissue are unable to comply with the task assigned to them in the tumor tissue, by which means the increase in tissue volume and/or the metastasis of the tumor is at least partially inhibited.

In another preferred embodiment of the invention, the active ingredient is directed against activators, inhibitors, regulators and/or biological precursors of proteins synthesized and/or secreted by tumors. These activators, inhibitors, regulators and/or biological precursors may be for example members, located up- and downstream, of the transduction cascade of the proteins listed in table I, transcription factors which regulate the level of expression of said proteins, but also previously unknown molecules which are influenced by the active ingredient and are involved in the expression and/or function of said proteins.

It is possible in the invention to use both known and unknown active ingredients or substances. Thus, for example, the active ingredient or the substance may be a polynucleotide which encodes a peptide, in particular a polypeptide, this peptide preferably influencing, in particular inhibiting, the expression and/or function of proteins synthesized and/or secreted by tumors. The active ingredient or the substance may further be a peptide, preferably a polypeptide, this peptide preferably influencing, in particular inhibiting, the expression and/or function of proteins synthesized and/or secreted by tumors. The active ingredient or the substance may further be a small molecular compound, preferably a small molecular compound having a molecular weight (MW) of <1000.

In a particularly preferred embodiment, the malignant tumor is a prostatic carcinoma. As already described, prostatic carcinomas represent the commonest malignant tumors in men. Only if a prostatic tumor can be detected in an early stage e.g. by prostate-specific antigen-based mass screenings (Bartsch G, Horninger W, Klocker H, Reissigl A, Oberaigner W, Schonitzer D, Severi G, Robertson C, Boyle P: Prostate cancer mortality after introduction of prostate-specific antigen mass screening in the Federal State of Tyrol, Austria. Urology 2001; 58:417-24) is it possible to consider the pure (preventive) surgical removal of the prostate (Bukkapatnam R, Pow-Sang J M: Radical prostatectomy in the management of clinically localized prostate cancer. Cancer Control 2001; 8:496-502; Pentyala S N, Lee J, Hsieh K, Waltzer W C, Trocchia A, Musacchia L, Rebecchi M J, Khan S A: Prostate cancer: a comprehensive review. Med Oncol 2000; 17:85-105). For the advanced disorder which is no longer limited to one organ, preventive removal of the prostate is no longer adequate. A possible choice of therapy for these prostatic tumors (prostatic carcinomas), some of which are inoperative, is, as already described, inhibition of the male sex hormones (Hussain A, Dawson N: Management of advanced/metastatic prostate cancer: 2000 update. Oncology (Huntingt) 2000; 14; 1677-88; discussion 1688, 1691-4). This inhibition of the production of male sex hormones, in some cases in combination with surgical or pharmacological castration, partly inhibits the proliferation and metastasis of the tumor and thus permits it to be controlled for a certain period (Afrin L B, Ergul S M: Medical therapy of prostate cancer: 1999. J S C Med Assoc 2000; 96:77-84; Auclerc G, Antoine E C, Cajfinger F, Brunet-Pommeyrol A, Agazia C, Khayat D: Management of advanced prostate cancer. Oncologist 2000; 5:36-44). Most prostatic tumors develop over time a certain resistance to this endocrinological therapy and, over time, they become androgen-insensitive (Eder I E, Culig Z, Putz T, Nessler-Menardi C, Bartsch G, Klocker H: Molecular biology of the androgen receptor: from molecular understanding to the clinic. Eur Urol 2001; 40:241-51; Crawford E D, Rosenblum M, Ziada A M, Lange P H: Hormone refractory prostate cancer. Urology 1999; 54:1-7). Further possible therapeutic options such as, for example the use of cytotoxic agents (Heidenreich A, von Knobloch R, Hofmann R: Current status of cytotoxic chemotherapy in hormone refractory prostate cancer: Eur Urol 2001; 39:121-30), gene therapy (Miyake H, Hara I, Kamidono S, Gleave M E: Novel therapeutic strategy for advanced prostate cancer using antisense oligodeoxynucleotides targeting anti-apoptotic genes upregulated after androgen withdrawal to delay androgen-independent progression and enhance chemosensitivity. Int J. Urol 2001; 8:337-49) and immunotherapy (Rini B I, Small E J: Immunotherapy for prostate cancer. Curr Oncol Rep 2001; 3:418-23), although undergoing clinical testing, have not to date been able to achieve significant success in the treatment of prostatic carcinoma (DiPaola R S, Kumar P, Hait W N, Weiss R E: State-of-the-art prostate cancer treatment and research. A report from the Cancer Institute of New Jersey. N J Med 2001; 98:23-33). Identification of genes which are expressed only in tumors, or in which different expression can be detected in benign and malignant tumors, is therefore a promising approach to the therapy of these tumors (Magee J A, Araki T, Patil S, Ehrig T, True L, Humphrey P A, Catalona W J, Watson M A, Milbrandt J: Expression profiling reveals hepsin overexpression in prostate cancer. Cancer Res 2001; 61:5692-6; Welsh J B, Sapinoso L M, Su AI, Kern S G, Wang-Rodriguez J, Moskaluk C A, Frierson H F, Jr., Hampton G M: Analysis of gene expression identifies candidate markers and pharmacological targets in prostate cancer. Cancer Res 2001; 61:5974-8; Stamey T A, Warrington J A, Caldwell M C, Chen Z, Fan Z, Mahadevappa M, McNeal J E, Nolley R, Zhang Z: Molecular genetic profiling of Gleason grade 4/5 prostate cancers of compared to benign prostatic hyperplasia. J Urol 2001; 166:2171-7; Dhanasekaran S M, Barrette T R, Ghosh D, Shah R, Varambally S, Kurachi K, Pienta K J, Rubin M A, Chinnaiyan A M: Delineation of prognostic biomarkers in prostate cancer. Nature 2001; 412: 822-6; Waghray A, Schober M, Reroze F, Yao F, Virgin J, Chen Y Q: Identification of differentially expressed genes by serial analysis of gene expression in human prostate cancer. Cancer Res 2001; 61:4283-6; Chaib H, Cockrell E K, Rubin M A, Macoska J A: Profiling and verification of gene expression patterns in normal and malignant human prostate tissues by cDNA microarray analysis. Neoplasia 2001; 3:43-52; Chetcuti A, Margan S, Mann S, Russell P, Handelsman D, Rogers J, Dong Q: Identification of differentially expressed genes in organ-confined prostate cancer by gene expression array. Prostate 2001; 47:132-40). It is therefore possible according to the invention to offer a therapeutic approach to the treatment of these tumors through inhibition of the described tumor-associated proteins.

The active ingredient or the substance can moreover be administered orally, intravenously, topically and/or by inhalation in a further preferred embodiment. The administration form depends on the tumor itself and on the patient's constitution. Further administration forms are known to the skilled worker.

The invention additionally includes a pharmaceutical composition which comprises an effective amount of at least one active ingredient which influences, in particular inhibits, the expression and/or the function of proteins synthesized and/or secreted by tumors, in particular by malignant tumors, and where appropriate a pharmaceutical carrier. The active ingredient may be a polynucleotide which encodes a peptide, in particular a polypeptide, this peptide preferably influencing, in particular inhibiting, the expression and/or function of proteins synthesized and/or secreted by tumors, in particular malignant tumors. The active ingredient may further be a peptide, preferably a polypeptide, this peptide preferably influencing, in particular inhibiting, the expression and/or function of proteins synthesized and/or secreted by tumors, in particular malignant tumors. The active ingredient may also be a so-called small molecular compound, preferably a small molecular compound having a molecular weight (MW) of <1000. For the further features of such an active ingredient, reference is made to the corresponding previous text of the description.

The invention also encompasses a pharmaceutical composition which comprises an effective amount of at least one active ingredient which influences, in particular inhibits, the expression and/or function of activators, inhibitors, regulators and/or biological precursors of proteins synthesized and/or secreted by tumors, in particular malignant tumors, and where appropriate a pharmaceutical carrier. The active ingredient in this case may be a polynucleotide which encodes a peptide, preferably a polypeptide, this peptide preferably influencing, in particular inhibiting, the expression and/or function of activators, inhibitors, regulators and/or biological precursors of proteins synthesized and/or secreted by tumors, in particular malignant tumors. The active ingredient may also be a peptide, preferably a polypeptide, this peptide preferably influencing, in particular inhibiting, the expression and/or function of activators, inhibitors, regulators and/or biological precursors of proteins synthesized and/or secreted by tumors, in particular malignant tumors. A further active ingredient of the invention may be for example a small molecular compound, preferably a small molecular compound having a molecular weight (MW) of <1000. For the further features of such an active ingredient, and of the activators, inhibitors, regulators and/or biological precursors against which this active ingredient is directed, reference is made to the corresponding previous text of the description.

Finally, the invention includes a diagnostic kit, this diagnostic kit comprising at least one substance for detecting the expression and/or function of proteins synthesized and/or secreted by tumors, in particular malignant tumors, for diagnosing disorders associated with these tumors. It is moreover possible for example for a corresponding disorder to be a prostatic carcinoma, which is claimed in a particularly preferred embodiment. For further features of such a substance, reference is made to the corresponding previous text of the description.

The existing features and further features of the invention are evident from the following description of preferred embodiments in conjunction with the dependent claims and the figures. It is possible in this connection for the individual features to be implemented each on its own or in a combination of a plurality with one another.

The patent or application file contains at least one drawing executed in color. Copies of this patent or patent application publication with color drawings will be provided by the Office upon request and payment of the necessary fee.

The figures show:

FIG. 1: Diagrammatic representation of the experimental design

Figure 2:
Figure 2:

FIG. 2: Gel electrophoretic and MS analysis of benign and malignant prostatic tissue and the equivalent spots.

FIG. 3: Preparative gels with tissue-specific protein expression.

MATERIAL AND METHODS

Patients and Tissue Samples

Benign and malignant prostatic tissue were obtained from patients previously subjected to a prostatectomy. The patients had been identified with the aid of PSA (prostata specific antigen) screening, and the tumors were confirmed with ultrasound. Consent was obtained from each patient before the operation was performed.

Immediately after the prostate was removed it was transferred into a sterile box and cooled therein. The samples were transferred to the pathologist, where tissue sections 0.5 to 1 cm thick were made. The sections were divided into a left and a right half, embedded in a freezing matrix and shock-frozen. The remainder of the prostate was fixed in formalin and treated further in accordance with standard methods. To obtain tissue samples, thin sections were taken from both sides of the prostate and stained with hematoxilin-Eosin. The pathologist located and marked the tumor. Tumor tissue was taken from the hematoxilin-Eosin-stained strips and stored at −80° C. Marked benign control strips were taken from regions not affected by tumor and subjected to an identical treatment. The tumors were stored at −80° C. where necessary.

Proteomics Analysis:

Protein alkylation, iodination, 2D-PAGE and the data analysis were carried out in accordance with standard methods. Radioactive iodine originates from Amersham Biosciences (Freiburg). Proteins were labeled with iodine I-125 or I-131 singly with identical concentrations of iodine. All radioactive operations were generated in accordance with the "Radiation protection regulations 2001" (Germany). For the 2D PAGE, the samples were mixed together and fractionated by co-electrophoresis in accordance with the diagram of FIG. 1. The radioactive measurements were carried out with a multiple photon detection (MPD) or a Phosphorimager (Fuji FLA 3000, Raytest, Straubenhard, Germany).

The multiple photon detection measurements were carried out on a 1600 pixel MPD imager (BioTracers Inc., Herndon, USA) in accordance with the manufacturer's instructions for at least 24 hours, for a 24 cm×24 cm region per measurement. The scanning in these cases was set at 0.5 mm per pixel. In some cases, small regions were scanned for a longer time in order to achieve a higher sensitivity, or scanning was at 0.25 mm per pixel in order to increase the resolution. The MPD imagers were moreover set to detect either I-125 or I-131 in each measurement. Because of the shorter half-life of I-131, this isotope was always measured before I-125 for each individual sample. MPD data were converted into matrix data using the IMAGEVIEW software (BioTraces). These data were then analyzed using the BIOPREPARATION software in accordance with the manufacturer's instructions. Radioactive data were converted into TIFF data with the aid of an algorithm for analysis of conventional software. Some radioactive measurements were carried out with a Phosphorimager.

Protein identification was carried out using preparative 2D PAGE gels. These gels contain up to 1 mg of protein which have been iodinated under identical chemical conditions as for the radioactive iodination, but with addition of non-radioactive iodine molecules. Silver-stained proteins with a migration behavior like the radioactive proteins were collected automatically with the aid of the Genomic Solutions Flexys robot. In some cases, the silver-stained proteins were removed at the places on the gel where no radioactive signal was present but where the silver gels differed between benign and malignant tissue. Gel portions were digested automatically with trypsin in a Genomic Solutions Investigator Progest and 10% of the resulting proteins were loaded onto a MALDI template with the aid of a Genomic Solutions Investigator ProMS robot. MALDI-TOF was carried out in a Bruker AutoFlex in accordance with the manufacturer's information. Where necessary, up to 90% of the peptide obtained by trypsin digestion was analyzed with the aid of the LC/MS/MS method. In this case, an LC-Packing Ultimate micro HPLC was connected to a Bruker Esquire ion trap mass spectrometer, or the samples were analyzed with the aid of the nanospray MS/MS method on the same mass spectrometer. Protein identification was carried out with the aid of the MASCOT program of version 1.07 (Matrix Science, UK) using our own algorithms.

Results:

FIG. 1 shows a diagrammatic representation of the experimental design on which the results are based. This entails two samples A and B to be analyzed each being labeled separately with I-125 and I-131 in order to obtain the iodinated samples 125-A, 125-B, 131-A and 131-B. Each sample is analyzed in gels 1 and 2 in each case comparing with the same but differently labeled sample, as also depicted in the figures. Samples A and B are analyzed in gels 3 and 4, comparing with the corresponding other sample under the same conditions. These gels therefore contain four replicates of samples A and B, these being directly related to samples A and B.

FIG. 2 shows the results of these experiments. FIG. 2A therein represents malignant, 2 B benign and 2 C the comparative gel (2 A+2 B). FIG. 2C shows the different expression of individual proteins in the different tissues. The results of these analyses are compiled in table I which has already been shown.

FIG. 3 shows the proteins found for the example of two preparative gels (pH range 4-10). It should be pointed out in particular that several isoforms of individual proteins were found. Thus, for example, a total of 5 isoforms which were detected at pH 6.5-7.5 exist for protein 11 (gamma-seminoprotein), thus demonstrating the existence of several isoforms of one and the same protein. It was additionally possible to show that there is formation not only of particular proteins but in particular also of specific isoforms of individual proteins in tumors. It is also possible to show that in some cases the expression of particular proteins (see table I) is inhibited, i.e. downregulated. These proteins thus represent suitable targets for known and yet to be developed active ingredients for the treatment of the disorders associated therewith, and suitable targets for detecting these disorders.

The invention claimed is:

1. A method for diagnosing prostatic carcinomas in a patient, comprising contacting prostate tissue from said patient with an antibody which is directed against proteins synthesized and/or secreted by carcinomas, wherein the proteins are selected from the group consisting of sialic acid synthase (SEQ ID NO:1) and KNP-I beta (SEQ ID NO:2), and wherein a higher level of said proteins in said prostate tissue, as compared to the level of said proteins in normal prostate tissue, indicates said patient has a prostatic carcinoma.

* * * * *